United States Patent
Biassoni et al.

(10) Patent No.: US 7,384,631 B2
(45) Date of Patent: Jun. 10, 2008

(54) METHODS OF DIAGNOSIS AND TREATMENT BY BINDING P75/AIRM1

(75) Inventors: Roberto Biassoni, Genoa (IT); Alessandro Moretta, Genoa (IT); Lorenzo Moretta, Genoa (IT); Maria Cristina Mingari, Genoa (IT)

(73) Assignee: Universita Degli Studi Di Genova, Dipartimento Di Medicina Sperimentale, Genoa (IT)

( * ) Notice: Subject to any disclaimer, the term of this patent is extended or adjusted under 35 U.S.C. 154(b) by 408 days.

(21) Appl. No.: 10/149,593

(22) PCT Filed: Dec. 11, 2000

(86) PCT No.: PCT/EP00/12509

§ 371 (c)(1), (2), (4) Date: Oct. 2, 2002

(87) PCT Pub. No.: WO01/44808

PCT Pub. Date: Jun. 21, 2001

(65) Prior Publication Data

US 2003/0077285 A1   Apr. 24, 2003

(30) Foreign Application Priority Data

Dec. 16, 1999 (IT) .................. FI99A0254

(51) Int. Cl.
 *A61K 39/395* (2006.01)
(52) U.S. Cl. .................. 424/141.1; 530/388.1
(58) Field of Classification Search .................. 435/7.1, 435/7.23
See application file for complete search history.

(56) References Cited

U.S. PATENT DOCUMENTS 5,714,350 A    2/1998   Co
5,730,982 A    3/1998   Scheinberg

FOREIGN PATENT DOCUMENTS

EP    0 867 721 A1    9/1998
WO    WO 88/05783     8/1988

OTHER PUBLICATIONS

Nicoli et al. (Jnl. Biol. Chem. Nov. 26, 1999, vol. 274, No. 48, pp. 34089-34095).*
Raag et al. (FASEB Jnl. 1995, vol. 9, pp. 73-80).*
IHOP synonyms for p75/AIRM1.*
"Pluripotential hemopoietic stem cell" downloaded on Jun. 8, 2006, from url>wikipedia.org/wiki/Myeloid_cells#Myeloid.*
Vitale et al Proc. Natl. Acad. Sci (1999) 96(26), 15091-15096 XP002171141 Engagement of p75/AIRM1 or CD33 inhibits the proliferation of normal or leukemic myeloid cells.
Falco et al J. Exp. Med. (1999) 190(6), 793-801 Sep. 1999 XP002926725 Identification and molecular cloning of p75/AIRM1, A novel member of the sialoadhesin family that functions as an inhibitory receptor in human natural killer cells.
Mingari MC, Vitale C, Romagnani C, Falco M, Moretta L. Regulation of myeloid cell proliferation and survival by p75/AIRM1 and CD33 surface receptors. Adv Exp Med Biol. 2001; vol. 495; pp. 55 61.
Mingari MC, Vitale C, Romagnani C, Falco M, Moretta L. p75/AIRM1 and CD33, two sialoadhesin receptors that regulate the proliferation or the survival of normal and leukemic myeloid cells. Immunol Rev. Jun. 2001; vol. 181; pp. 260 268.
Vitale C, Romagnani C, Puccetti A, Olive D, Costello R, Chiossone L, Pitto A, Bacigalupo A, Moretta L, Mingari MC. Surface expression and function of p75/AIRM 1 or CD33 in acute myeloid leukemias: engagement of CD33 induces apoptosis of leukemic cells. Proc Natl Acad Sci U S A. May 8, 2001; vol. 98(10); pp. 5764 5769.
GenBank AJ007395.1, Submitted Jun. 25, 1998, Biassoni et al.

* cited by examiner

*Primary Examiner*—Misook Yu
(74) *Attorney, Agent, or Firm*—Nixon & Vanderhye P.C.

(57) ABSTRACT p75/AIRM1 is expressed on myeloid cells at stages of differentiation and determination of its presence is useful in monitoring cellular proliferation and determining proliferative states of cells, especially myeloid cells in diseases such as chronic myeloid leukemia. Ligands such as antibody molecules, for instance the QA79 monoclonal antibody deposited under accession number ICLC No. PD99003, are useful for methods of diagnosis and treatment, e.g. by way of inhibition of cellular proliferation and induction of apoptosis in cells.

6 Claims, No Drawings

METHODS OF DIAGNOSIS AND TREATMENT BY BINDING P75/AIRM1

The present application is a 371 U.S. National Phase of PCT/EP00/2509, filed Dec. 11, 2000.

The present invention relates to cellular proliferation, in particular disorders of cellular proliferation such as leukemia, methods of monitoring proliferation and determining proliferative states of cells, identifying normal and abnormal cells, e.g. leukemic myelomonocytic cells, at different stages of maturation, methods of diagnosis and treatment, and reagents including ligands for use in such methods. The invention is based in part on identification of ligands specific for a newly characterized and cloned cell surface receptor, p75/AIRM1, and experimental results showing expression of p75/AIRM1 on myeloid cells at stages of differentiation, and use of ligands directed against the receptor for inhibition of cellular proliferation and induction of apoptosis in cells.

It is known that normal hemopoiesis is a multistep process in which cellular differentiation depends on different growth factors and on the expression of defined transcription factors. The process is characterized by the sequential expression of cell surface markers that allow the recognition of different stages of cellular differentiation. For example, cells expressing the CD34 surface marker include pluripotent hemopoietic germinal cells, while CD33 is absent on such germinal cells. On the other hand, CD33 is expressed on myelomonocytic precursors, as well as on myeloid and monocytic cells, while it disappears on mature granulocytes.

Although CD33 is a useful marker to distinguish myeloid from lymphoid leukemias, very little is known about its function.

In the work described in Falco et al., Journal Experimental Medicine vol. 90, No. 06, 20 Sep. 1999, page 793-802, an inhibitory receptor expressed on Natural Killer (NK) cells able to regulate NK cell functions was identified and characterized in the laboratories of the present inventors. The complete amino acid sequence (SEQ ID NO:1) of this receptor, termed p75/AIRM1 (75 kD adhesion inhibitory receptor molecule 1), and encoding nucleotide sequence therefor, is shown in FIG. 5 of Falco et al, which document is incorporated herein by reference, along with all other publications mentioned herein.

CD33 myeloid cell antigen and p75/AIRM1 share amino acid sequence identity with each other. CD33 is known to be selectively expressed by hemopoietic cells. It represents an important marker to study myeloid differentiation and for typing and staging leukemias. A monoclonal antibody specific for CD33 has been recently utilized in the therapy of acute pro-myelocytic cell leukemias (Caron et al.: Cancer 73, 1049-56 1994; Clin. Cancer Res. 1, 63-70, 1995 and ibidem 4, 1421- 28, 1998)

Unpredictably, it has been demonstrated by the present inventors that the use of ligands, such as antibody molecules, enables the identification of particular stages of differentiation of myeloid cells. More importantly, this receptor is expressed in myeloid cell differentiation later than CD33, being extremely useful for diagnosis and therapeutic treatments, e.g. of leukemias, especially CML and AML. The identification of the p75/AIRM1 receptor makes possible a more precise definition of the different maturative stages of myeloid cells. This will be useful for an accurate typing of leukemias, with anticipated benefits for their prognosis and therapeutic treatment.

Preferred embodiments of the various aspects of the present invention employ antibody molecules with the binding characteristics of the QA79 monoclonal antibody (mAb) specific for the QA79-p75/AIRM1 receptor (hybridoma that produces QA79 deposited by Professor Alessandro Moretta of DIMES (Dipartimento di Medicina Sperimentale, Sezione di Patologia Generale, Universita Degli Studi Di Genova, Via L. B. Alberti 2, 16132 GENOVA, Italia—the present applicant) on behalf of the present applicant, at the Interlab Cell Line Collection, Centro di Biotecnologie Avanzate (CBA), Servizio Biotecnologie, L.go R. Benzi, 10, 16132 GENOVA, Italia, on 10 Dec. 1999 and given accession number ICLC No. PD99003). The generation of the QA79 mAb is detailed below.

Another more important effect of the use of a ligand such as an antibody molecule is demonstrated by the fact that upon interaction of an antibody such as QA79 with the p75/AIRM1 receptor molecules, myeloid cells undergo a proliferative arrest and programmed cell death or apoptosis is induced. This effect has been documented in vitro both on normal and myeloid leukemic cells, and it gives important molecular basis for therapeutic intervention directed to eliminate leukemic cells (e.g. leukemic cells left after chemotherapy).

The present invention in various aspects to methods to identify normal and leukemic myeloid cells by the use of specific ligands for the p75/AIRM1, to such ligands and to their diagnostic and therapeutic use.

Ligands useful in accordance with the present invention are generally antibody molecules, and may be murine monoclonal antibodies or their "humanized" forms, or fragments such as soluble recombinant molecules (e.g. single chain Fv, or ScFv, antibody molecules). Furthermore, other useful ligands include all the other molecules able to recognize and/or specifically bind to the p75/AIRM1 receptor molecules, such as peptides and pharmaceutical formulations.

An antibody molecule is an immunoglobulin whether natural or partly or wholly synthetically produced. Examples of antibody molecules are the immunoglobulin isotypes and their isotypic subclasses; fragments which comprise an antigen binding domain such as Fab, scFv, Fv, dAb, Fd, and diabodies. As antibodies can be modified in a number of ways, the term "antibody molecule" should be construed as covering any polypeptide comprising an immunoglobulin antigen-binding domain, whether natural or wholly or partially synthetic. Chimeric molecules comprising an immunoglobulin antigen-binding domain fused to another polypeptide are therefore included. In addition to antibody sequences, the specific binding member may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or enzyme (e.g. via a peptidyl bond or linker). A ligand, such as antibody molecule, may in accordance with the present invention be provided as part of a conjugate comprising a radioisotope, or toxin, emitoxin or other compound able to potentiate cytotoxic effect, e.g. in an anti-leukemic context.

Cloning and expression of chimeric antibodies are described for example in EP-A-0120694, EP-A-0125023 and EP-A-0451216.

"Antigen-binding domain" describes the part of an antibody molecule which comprises the area which specifically binds to and is complementary to part or all of an antigen. Where an antigen is large, an antibody may only bind to a particular part of the antigen, which part is termed an epitope. An antigen-binding domain may be provided by one or more antibody variable domains (e.g. a so-called Fd antibody fragment consisting of a VH domain). Preferably, an antigen-binding domain comprises an antibody light chain variable region (VL) and an antibody heavy chain variable region (VH).

A ligand that is "specific" for a binding partner will not generally show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" is generally used in the sense of "include", that is to say permitting the presence of one or more features or components.

The term "isolated" is used to refer to the state in which ligands such as antibody molecules of the invention, or nucleic acid encoding such binding members, are generally employed in accordance with the present invention. This means the relevant ligand or nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. A ligand or nucleic acid may be formulated with diluents or adjuvants and still for practical purposes be "isolated"—for example a ligand will normally be mixed with gelatin or other carriers if used to coat microtitre plates for use in immunoassays, or will be mixed with pharmaceutically acceptable carriers or diluents when used in diagnosis or therapy.

A preferred antibody molecule ligand according to the present invention comprises the antigen-binding domain of the QA79 antibody, available from the Interlab Cell Line Collection under accession number ICLC No. PD99003 (depositary details of which are given above). This is a mouse monoclonal antibody and using only routine experimental techniques an ordinary skilled person is well able to isolate from the deposited hybridoma cells the antibody light and heavy chain encoding sequences. These may readily be used in recombinant expression systems for production of the antibody. Furthermore, the nucleic acid encoding the QA79 VH and VL variable regions may easily be used to construct sequences encoding antibody molecules such as scFv, Fv and Fab antibody molecules, which molecules can be produced by recombinant expression in accordance with any of a variety well-established techniques at the disposal of the ordinary skilled person.

The present invention provides as further aspects any specific binding member or ligand comprising a VH and/or VL domain which comprises the amino acid sequence of the VH and/or VL domain of the QA79 antibody molecule, obtainable from the deposit as disclosed. Such a specific binding member or ligand may be a whole antibody, or may be a scFv, Fv or Fab antibody molecule.

Antibody molecule ligands of the present invention may comprise antibody constant regions or parts thereof. For example, a VL domain may be attached at its C-terminal end to antibody light chain constant domains including human Cκ or Cλ chains, preferably Cλ chains. Similarly, a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4.

According to a further aspect of the invention there is provided a method for the generation and isolation of a monoclonal antibody, the method comprising:

a) immunising a Balb/c mouse with cells derived from a human NK cell clone with surface phenotype: CD3⁻ CD16⁺, CD56⁺, NKp46⁺, NKp44⁺, p140⁺, CD94/NKG2A⁺;
b) isolating murine splenocytes and fusing them with the murine (e.g. P3V1) myeloma cell line to provide hybrid cells;
c) growing the hybrid cells in a 37° C. tissue culture incubator in the presence of 5% $CO_2$;
d) cloning cells in limiting dilutions to identify and isolate desired monoclonal antibody;
e) purifying hybrid supernatant and concentrating with ammonium sulphate (40%) and anionic exchange chromatography.

Furthermore, since the skilled person is well able to humanise the QA79 mouse monoclonal antibody or other non-human antibody molecule, by transferring the CDR sequences into a human framework and making as necessary one or more changes to the sequence of human framework, most likely at a few well-known residues, including canonical residues noted for influence on CDR structure and therefore antibody antigen-binding characteristics (including specificity and affinity), the present invention further provides as another aspect a humanised antibody VH domain comprising one or more CDR's of the QA79 VH domain, preferably all three of CDR's 1, 2 and 3; further provides a humanised antibody VL domain comprising one or more CDR's of the QA79 VL domain, preferably all three of CDR's 1, 2 and 3; and further provides a humanised antibody molecule comprising an antibody VH domain comprising one or more CDR's of the QA79 VH domain, preferably all three of CDR's 1, 2 and 3, and an antibody VL domain comprising one or more CDR's of the QA79 VL domain, preferably all three of CDR's 1, 2 and 3.

The present invention further extends to a specific binding member or ligand which competes with the QA79 antibody molecule for binding to p75/AIRM1, especially but not necessarily any antibody molecule which both binds the p75/AIRM1 antigen and comprises a variable domain comprising a CDR of QA79. Competition between binding members may be assayed easily in vitro, for example by tagging a specific reporter molecule to one binding member (e.g. antibody molecule) which can be detected in the presence of other untagged binding member(s) (e.g. antibody molecule(s)), to enable identification of ligands which bind the same epitope or an overlapping epitope.

In testing for competition a peptide fragment of the antigen may be employed, especially a peptide including an epitope of interest. A peptide may have the epitope sequence plus one or more amino acids at either end, may be used. Such a peptide may be said to "consist essentially" of the specified sequence. Specific binding members or ligands according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s) or with the ectodomain of p75/AIRM1 obtained using recombinant techniques. A human antibody against p75/AIRM1 may be obtained from such a library, and if preferred a human antibody may be obtained that competes with the QA79 antibody for binding to p75/AIRM1, although antibody molecules, e.g. human antibody molecules, that bind other regions or epitopes of p75/AIRM1 are provided by and are useful in various aspects and embodiments of the present invention.

Variants of the QA79 VH and VL domains may be employed in ligands of the invention, and can be obtained by means of methods of sequence alteration or mutation and screening. Such methods are also provided by the present invention.

Variable domain amino acid sequence variants of the QA79 VH and/or VL domains may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

Antibody molecules and other ligands of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin. Other approaches for labelling antibody molecules and other ligands are discussed further below, along with additional explanation of ligand use in assays, such as diagnostic assays, which may be carried out in vitro or in vivo.

Since a convenient way to make an antibody molecule according to the present invention may employ recombinant expression from suitable encoding nucleic acid, a further aspect of the present invention provides nucleic acid, generally isolated, encoding an antibody VH variable domain and/or VL variable domain according to the invention.

Another aspect of the present invention provides nucleic acid, generally isolated, encoding a VH CDR3 sequence of the QA79 antibody molecule or other antibody molecule according to the invention. In generating a humanised antibody molecule or other CDR-grafted antibody molecule using QA79, for instance, it may be that only the VH CDR3 sequence is transferred, other CDR's being of lesser importance in determining binding characteristics. The QA79 VH CDR3, for example, may be grafted into an otherwise wholly human framework, or a diverse population of otherwise wholly human frameworks from which an antibody molecule with desired properties (including specificity for p75/AIRM1) may be selected.

Nucleic acid according to the present invention may be DNA or RNA. The present invention also provides constructs in the form of plasmids, vectors, transcription or expression cassettes which comprise at least one nucleic acid or polynucleotide as above.

The present invention also provides a recombinant host cell which comprises one or more constructs as above. Expression may conveniently be achieved by culturing under appropriate conditions recombinant host cells containing the nucleic acid. Following production by expression, the product may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells (CHO cells), NS0 (ECACC 85110503) cells, HeLa cells, baby hamster kidney cells, and many others. A common, preferred bacterial host is E. coli.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual*: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or ligand as above.

A yet further aspect provides a method of production of a ligand according to the present invention, the method comprising causing expression from nucleic acid that encodes the ligand. Such a method may comprise culturing host cells under conditions for production of the encoded polypeptide product. A method of production may comprise a step of isolation and/or purification of the product.

A method of production may comprise formulating the product into a composition including at least one additional component, such as a pharmaceutically acceptable excipient.

In embodiments of the present invention, ligands such as antibody molecules of the present invention may be used in methods of diagnosis or treatment in human or animal subjects, preferably human.

Accordingly, further aspects of the invention provide methods of treatment comprising administration of a specific binding member or ligand as provided, pharmaceutical compositions comprising such a specific binding member or ligand, and use of such a specific binding member or ligand in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

A composition may be administered alone or in combination with other treatments, either simultaneously or sequentially dependent upon the condition to be treated.

Antibodies of the present invention may be administered to a patient in need of treatment via any suitable route, usually by injection into the bloodstream or directly into the site to be treated, e.g. tumor. The precise dose will depend upon a number of factors, including whether the antibody is for diagnosis or for treatment, the size and location of the area to be treated, the precise nature of the antibody (e.g. whole antibody or fragment), and the nature of any detectable label or other molecule attached to the antibody. A typical antibody dose will be in the range 0.5 mg to 100 g for systemic applications, and 10 μg to 1 mg for local applications. Typically, the antibody will be a whole antibody, e.g. the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Specific binding members, ligands and antibody molecules of the present invention will when administered usually be administered in the form of a pharmaceutical composition, which may comprise at least one component in addition to the specific binding member, ligand or antibody molecule.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. asprin, paracetamol, ibuprofen or ketoprofen) or opitates such as morphine, or anti-emetics.

The present invention provides a method comprising causing or allowing binding of a specific binding member or ligand as provided herein to its antigen. As noted, such binding may take place in vivo, e.g. following administration of a specific binding member or ligand, or nucleic acid encoding a specific binding member or ligand, or it may take place in vitro, for example in ELISA, Western blotting, immunocytochemistry, immuno-precipitation or affinity chromatography.

The amount of binding of specific binding member to antigen may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member or ligand, especially a QA79 antibody molecule as above, for measuring antigen levels in a competition assay, that is to say a method of measuring the level of antigen in a sample by employing a specific binding member or ligand as provided by the present invention in a competition assay. This may be where the physical separation of bound from unbound antigen is not required. Linking a reporter molecule to the specific binding member or ligand so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody molecule and reporter molecule.

The mode of determining binding is not a feature of the present invention and those skilled in the art are able to choose a suitable mode according to their preference and general knowledge.

Further aspects and embodiments of the present invention will be apparent to those skilled in the art, in view of the following experimental exemplification and support.

EXPERIMENTAL DESCRIPTION

Isolation of a Monoclonal Antibody Against p75/AIRM1

The QA79 mAb of IgG1 isotype was obtained by immunizing a 5 weeks old BALB/c mouse with an NK cell clone (clone LM5 expressing a $CD3^-$ $CD16^+$, $CD56^+$, $NKp46^+$, $NKp44^+$, $p140^+$, $CD94/NKG2A^+$ phenotype).

In more detail, immunization was performed with 4 weekly intraperitoneal injections and a fifth one after three days. The mouse was sacrificed after three more days. Each immunization was performed using 7 million of NK cells. Murine splenocytes isolated from the immunized mouse were fused with the murine myeloma cell line (P3V1) in order to obtain cell hybrids. 15 million splenocytes and the same number of P3V1 cells were treated with 0.4 ml polyethylene glycol MW 1500 (PEG 1500) added slowly, drop by drop, always keeping cells in suspension.

Next, 5 ml of tissue culture growing media (RPMI) pre-heated at 37° C. and 43 ml of the same RPMI supplemented with fetal bovine serum (FCS) to the final concentration of 10% were added slowly as above. The cell suspension in RPMI as described above was transferred in 24 wells tissue culture plates (0.5 ml/well) containing, complete growing media (0.5 ml of 10% FCS in RPMI supplemented with antibiotics) and in the presence of plastic adherent murine macrophages. Cells were cultured in a 37° C. incubator for tissue cultures in the presence of 5% $CO_2$. The next day, 1 ml of complete growing media supplemented of 13.6 mg/ml Ipoxantine, 0.238 mg/ml aminopterine and 0.238 mg/ml deoxythymidine (HAT: formulation of selective agents in which only hybrid cells can grow) were added to each well. In the next 10 days, the growing media always supplemented with HAT were changed every 3 days and weekly thereafter Next, hybrid culture supernatants were analyzed: (1) by indirect immunofluorescence to evaluate the isotype and the reactivity of the antibody; (2) in cytolytic functional assays to evaluate the possible function of the receptor recognized by the antibody produced by the hybrid(s). Later the selected hybrids were cloned in limiting dilution to obtain a hybrid clone producing a single antibody (in particular the QA79 monoclonal antibody).

The QA79 hybridoma was deposited at the Interlab Cell Line Collection on 10 Dec. 1999 and given accession number ICLC No. PD99003. Additional details on depositor and depositary have been given already above.

To produce an appropriate amount of mAb, BALB/c mice were inoculated with hybrid cells intraperitoneally (i.p.) after 2 weekly pretreatment with pristane. One week after the last pristane treatment, mice were injected with 6 million cells of the QA79 hybrid. Ten days later ascitic fluids were collected. The ascites were purified by ammonium sulfate precipitation (40% final concentration) and the pellet containing the QA79 mAb resuspended and purified by anionic exchange chromatography.

Reactivity of QA79 Antibody Molecule on Cells

In agreement with previous data, FACS analysis of cells gated on lymphoid populations indicated that p75/AIRM1 is expressed on NK cells, but not $CD3^+$ cells. Analysis of cells gated on myeloid populations showed that p75/AIRM1 is expressed by most $CD33^+$ cells and by the majority of $CD14^+$ cells. Whereas CD33 was found in variable proportions or not at all on isolated $CD34^+$ cells, p75/AIRM1 was consistently absent in $CD34^+$ populations, this providing indication that p75/AIRM1 is expressed later than CD33 during myeloid cell development. This was confirmed by experiments in which $CD34^+$ populations were cultured with SCF and GM-CSF and analysed for expression of the two markers, CD33 and p75/AIRM1.

Induction of Programmed Cell Death and of Inhibition of Cell Proliferation, in Normal and Leukemic Myeloid Cells, by the use of the QA79 mAb Specific for the p75/AIRM1 Receptor Molecules $CD34^+$ cord blood-derived cells were plated at the concentration of 20,000 cells/well in 96 flat-bottomed well plates and cultured in the presence of complete growing media supplemented with GM-CSF (100 ng/ml) and SCF (50 ng/ml). CML (chronic myeloid leukemia) cells were plated at final concentration of 50,000 cells/well in 6 flat-bottomed well plates and cultured in complete growing media supplemented only with GM-CSF (100 ng/ml). Both cell types, supplemented with the indicated growth factors, were also plated at the concentration of 20,000 cells/well in 96 flat-bottomed well plates coated with goat anti-mouse Ig (10 µg/ml).

Cells were cultured with saturating amounts of QA79 (anti-p75) or with other mAbs used as controls. At different time intervals (4, 6 and 8 days for cord blood-derived cells and 3, 4, 5 and 7 days for CML-derived cells), cells were harvested, counted, and analyzed for their surface phenotype. The proliferation assay was performed at the same interval as above, pulsing cells with 1 µCi/well [$^3$H] thymidine 16 hr before harvesting. Cells were harvested by using a Titertek cell harvester 550. Radioactivity was measured in a scintillation β-counter. All cultures were performed in triplicates.

Anti-p75/AIRM1 engagement, using QA79 mAb but not with mAbs used as controls, exerted a strong inhibitory effect on cell proliferation, both of normal myeloid cells and Chronic Myeloid Leukemias. Anti-p75-AIRM1 antibody has also been found to exert a strong inhibitory effect on cells samples of Acute Myeloid Leukemias with a high in vitro proliferation rate (cultured in the presence of granulocyte-macrophage-colony stimulating factor).

Among CML cells isolated from patients, maximal inhibition mediated by anti-p75/AIRM1 was observed for those cells showing the highest expression of the antigen.

The induction of programmed cell death was evaluated on the basis of annexin V surface reactivity. This is an indication of the beginning of the process of cell death by apoptosis. The expression of Annexin V was evaluated by the use of specific mAbs in indirect immunofluorescence and cytofluorimetric analysis. Cell surface binding with annexin V, changes in light scattering properties and nucleosomal DNA-fragmentation are indicative of the occurrence of apoptotic cell death.

The invention claimed is:

1. A method of determining the stage of differentiation of myeloid cells, the method comprising contacting myeloid cells in a sample with a ligand directed against p75/AIRM1 receptor (SEQ ID NO:1), and determining binding of the ligand, wherein an amount of binding is indicative of a stage of myeloid cellular differentiation which stage is later in development than the stage of myeloid cellular differentiation at which CD34 is expressed, and wherein the ligand is selected from the group consisting of: the QA79 monoclonal antibody produced from the hybridoma deposited as ICLC No. PD99003 or the antigen-binding fragment thereof which binds p75/AIRM1 (SEQ ID NO: 1); a humanised antibody comprising said antigen-binding fragment; and an isolated human antibody competing for the binding of the same epitope that the QA79 antibody binds to and the epitope is located on p75/AIRM1 (SEQ ID NO: 1).

2. A method according to claim 1 wherein the antibody molecule is a single chain Fv (scFv) antibody molecule.

3. QA79 monoclonal antibody produced from the hybridoma deposited as ICLC No. PD99003, the antigen-binding fragment which binds p75/AIRM1 (SEQ ID NO:1), a humanised antibody comprising said antigen-binding fragment, or an isolated human antibody competing for binding of the same epitope that the QA79 antibody binds to and the epitope is located on p75/AIRM1 (SEQ ID NO:1).

4. A method of determining the presence of p75/AIRM1 (SEQ ID NO: 1), which method comprises causing or allowing binding of a monoclonal antibody according to claim 3 and detecting any binding as an indication of the presence of p75/AIRM1.

5. A method according to claim 4 wherein said binding takes place in vitro.

6. A method according to claim 4 wherein the p75/AIRM1 (SEQ ID NO:1) is on the surface of myeloid cells.

* * * * *

SEQUENCE LISTING

<160> NUMBER OF SEQ ID NOS: 1

<210> SEQ ID NO 1
<211> LENGTH: 467
<212> TYPE: PRT
<213> ORGANISM: human

<400> SEQUENCE: 1

Met Leu Leu Leu Leu Leu Pro Leu Leu Trp Gly Arg Glu Arg Val
 1               5                  10                  15

Glu Gly Gln Lys Ser Asn Arg Lys Asp Tyr Ser Leu Thr Met Gln Ser
                20                  25                  30

Ser Val Thr Val Gln Glu Gly Met Cys Val His Val Arg Cys Ser Phe
            35                  40                  45

Ser Tyr Pro Val Asp Ser Gln Thr Asp Ser Asp Pro Val His Gly Tyr
        50                  55                  60

Trp Phe Arg Ala Gly Asn Asp Ile Ser Trp Lys Ala Pro Val Ala Thr
 65                 70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
        195                 200                 205

Gln His His Gly Thr Ser Leu Thr Cys Gln Val Thr Leu Pro Gly Ala
        210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
        290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

-continued

```
Leu Gly Ala Val Gly Ala Gly Ala Thr Ala Leu Val Phe Leu Ser
        355                 360                 365

Phe Cys Val Ile Phe Ile Val Val Arg Ser Cys Arg Lys Lys Ser Ala
        370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
                420                 425                 430

Arg Glu Ile Gln Tyr Ala Pro Leu Ser Phe His Lys Gly Glu Pro Gln
        435                 440                 445

Asp Leu Ser Gly Gln Glu Ala Thr Asn Asn Glu Tyr Ser Glu Ile Lys
        450                 455                 460

Ile Pro Lys
465
```